(12) United States Patent
Zhang

(10) Patent No.: US 11,977,064 B2
(45) Date of Patent: May 7, 2024

(54) METHOD AND APPARATUS FOR DETERMINING THE NITROGEN OXIDE CONCENTRATION AND A NITROGEN OXIDE RATIO IN THE EXHAUST GAS FLOW OF A MOTOR VEHICLE

(71) Applicant: Vitesco Technologies GmbH, Hannover (DE)

(72) Inventor: Hong Zhang, Munich (DE)

(73) Assignee: VITESCO TECHNOLOGIES GMBH, Hannover (DE)

( * ) Notice: Subject to any disclaimer, the term of this patent is extended or adjusted under 35 U.S.C. 154(b) by 677 days.

(21) Appl. No.: 17/259,481

(22) PCT Filed: May 16, 2019

(86) PCT No.: PCT/EP2019/062741
§ 371 (c)(1),
(2) Date: Jan. 11, 2021

(87) PCT Pub. No.: WO2020/011428
PCT Pub. Date: Jan. 16, 2020

(65) Prior Publication Data
US 2021/0278386 A1   Sep. 9, 2021

(30) Foreign Application Priority Data
Jul. 12, 2018   (DE) ..................... 10 2018 211 573.7

(51) Int. Cl.
*G01N 33/00* (2006.01)
*G01M 15/10* (2006.01)
*G01N 27/419* (2006.01)

(52) U.S. Cl.
CPC ...... *G01N 33/0062* (2013.01); *G01M 15/102* (2013.01); *G01N 27/419* (2013.01)

(58) Field of Classification Search
None
See application file for complete search history.

(56) References Cited

U.S. PATENT DOCUMENTS

| 2018/0113103 A1 | 4/2018 | Okamoto | G01N 33/00 |
| 2018/0142593 A1 | 5/2018 | Wang | F01N 3/20 |
| 2019/0128833 A1 | 5/2019 | Nakagaki | G01N 27/409 |

(Continued)

FOREIGN PATENT DOCUMENTS

| DE | 10 2008 006 633 | 7/2009 | ........... G01N 27/409 |
| DE | 10 2017 122 934 | 12/2017 | ............. F01N 11/00 |
| DE | 10 2017 007 601 | 4/2018 | ........... G01N 27/409 |

(Continued)

OTHER PUBLICATIONS

Search Report for International Application No. PCT/EP2019/062741, 14 pages, dated Sep. 30, 2019.

(Continued)

*Primary Examiner* — J. Christopher Ball
(74) *Attorney, Agent, or Firm* — Slayden Grubert Beard PLLC

(57) ABSTRACT

Various embodiments of the teachings herein include methods of ascertaining the nitrogen oxide concentration and a nitrogen oxide ratio in the exhaust gas stream from a motor vehicle comprising: measuring a pumping current and ascertaining the nitrogen oxide concentration and the nitrogen oxide ratio from at least three successive pumping current measurements.

11 Claims, 2 Drawing Sheets

(56) References Cited

U.S. PATENT DOCUMENTS

2019/0137441 A1    5/2019   Nakagaki ............. G01N 27/407

FOREIGN PATENT DOCUMENTS

| DE | 10 2017 127 509 | 5/2018  | ............... F01N 9/00 |
| EP | 3 477 291       | 5/2019  | ........... G01N 27/416 |
| JP | H 09-297119     | 11/1997 | ............. G01N 27/27 |
| WO | 2017 222001     | 12/2017 | ........... G01N 24/416 |
| WO | 2017 222002     | 12/2017 | ........... G01N 27/416 |

OTHER PUBLICATIONS

Office Action for DE Application No. 10 2018 211 573.7, 6 pages, dated May 24, 2019.
DIN 1319-3:1996-05—Grundlagen der Messtechnik Volltext, 24 pages, 1996.
Guardiola et al., "ECU-Oriented Models for $NO_x$ Prediction," *Journal of Automobile Engineering*, vol. 229(10), pp. 1345-1360, 2015.
Zhang et al., "Improved NO and $NO_2$ Concentration Estimation for a Diesel-Engine-Aftertreatment System," *IEEE/ASME Transactions on Mechatronics*, vol. 23, No. 1, pp. 190-199, Feb. 1, 2018.
Chinese Office Action, Application No. 201980046728.9, 14 pages, dated Sep. 2, 2022.

METHOD AND APPARATUS FOR DETERMINING THE NITROGEN OXIDE CONCENTRATION AND A NITROGEN OXIDE RATIO IN THE EXHAUST GAS FLOW OF A MOTOR VEHICLE

CROSS-REFERENCE TO RELATED APPLICATIONS

This application is a U.S. National Stage Application of International Application No. PCT/EP2019/062741 filed May 16, 2019, which designates the United States of America, and claims priority to DE Application No. 10 2018 211 573.7 filed Jul. 12, 2018, the contents of which are hereby incorporated by reference in their entirety.

TECHNICAL FIELD

The present disclosure relates to motor vehicles. Various embodiments of the teachings herein include methods and/or devices for ascertaining the nitrogen oxide concentration and a nitrogen oxide ratio in the exhaust gas stream from a motor vehicle.

BACKGROUND

WO 2017/222002 A1 describes a gas sensor and a method of measuring the concentrations of multiple components of a gas supplied. This gas sensor has three chambers arranged in succession, each connected to one another by a diffusion pathway. The first chamber is connected via a first diffusion pathway to a gas inlet, via which the gas sensor is supplied with the exhaust gas stream from a motor vehicle that includes nitrogen monoxide and nitrogen dioxide. In a first mode of operation of the gas sensor, in which the first chamber is deactivated, the exhaust gas stream passes through the first chamber unchanged and is guided via a second diffusion pathway into the second chamber. The nitrogen dioxide present in the exhaust gas stream is converted therein to nitrogen monoxide and oxygen. This nitrogen monoxide is supplied to the third chamber together with further nitrogen monoxide present in the exhaust gas stream. Nitrogen monoxide is converted therein to nitrogen and oxygen, and a pumping current is measured. In a second mode of operation of the gas sensor in which the first chamber is activated, the nitrogen dioxide present in the exhaust gas stream is converted to nitrogen monoxide and oxygen actually within this first chamber. This nitrogen monoxide is fed together with further nitrogen monoxide present in the exhaust gas stream via the second diffusion pathway to the second chamber, passes through the latter unchanged, and is supplied via the third diffusion pathway to the third chamber. Nitrogen monoxide is again converted therein to nitrogen and oxygen, and a pumping current is measured. Since the nitrogen monoxide transferred via the diffusion pathway envisaged between the first chamber and the second chamber and the nitrogen dioxide have different coefficients of diffusion in the two aforementioned modes of operation, a corresponding pumping current value measured in the third chamber is likewise different. The differential between the pumping current values measured, with use of empirically ascertained data recorded in a memory and recorded operating software, can be used to individually ascertain a corresponding nitrogen monoxide concentration and a corresponding nitrogen dioxide concentration.

SUMMARY

The teachings of the present disclosure include methods and devices for ascertaining a nitrogen oxide concentration and a nitrogen oxide ratio in the exhaust gas stream from a motor vehicle, which afford exact results even in dynamic operation of the motor vehicle. For example, some embodiments include a method of ascertaining the nitrogen oxide concentration and a nitrogen oxide ratio in the exhaust gas stream from a motor vehicle, in which the nitrogen oxide concentration and the nitrogen oxide ratio are ascertained from at least three successive pumping current measurements.

In some embodiments, every two successive pumping current measurements are measured in different modes of operation of a nitrogen oxide sensor (1).

In some embodiments, the successive pumping current measurements are measured by means of a nitrogen oxide sensor (1) having an inlet for an exhaust gas stream, and having three chambers (5, 9, 13) arranged in series, with every two successive chambers connected to one another via a diffusion pathway (8, 12).

In some embodiments, in a first mode of operation, nitrogen monoxide present in the exhaust gas stream and nitrogen dioxide present in the exhaust gas stream pass through the first chamber (5) unchanged and are supplied to the second chamber (9) via a diffusion pathway (8), the nitrogen dioxide present in the exhaust gas stream is converted to nitrogen monoxide in the second chamber (9), and the nitrogen monoxide is supplied together with the nitrogen monoxide present in the exhaust gas stream to the third chamber (13) via a further diffusion pathway (12), and a corresponding pumping current value is measured in the third chamber (13).

In some embodiments, in a second mode of operation, nitrogen dioxide present in the exhaust gas stream is converted to nitrogen monoxide in the first chamber (5), the nitrogen monoxide is supplied together with nitrogen monoxide present in the exhaust gas stream to the second chamber (9) via a diffusion pathway (8), the nitrogen monoxide supplied to the second chamber (9) passes through the second chamber (9) and is supplied to the third chamber (13) via a further diffusion pathway (12), and a corresponding pumping current value is measured in the third chamber (13).

In some embodiments, the nitrogen oxide concentration and the nitrogen oxide ratio are ascertained by means of a control unit (16) which is supplied with the at least three successive pumping current measurements.

In some embodiments, the control unit (16) ascertains the nitrogen oxide concentration and the nitrogen oxide ratio from four successive pumping current measurements, the first and third of which are measured in the first mode of operation and the second and fourth of which in the second mode of operation.

In some embodiments, the control unit (16) ascertains the nitrogen oxide concentration and the nitrogen oxide ratio on the basis of the following relationships:

$$NO\_2 + s1 \cdot NO2\_1 = y1,$$

$$NO\_2 + NO2\_2 = y2,$$

$$NO\_3 + s1 \cdot NO2\_3 = y3 \text{ and}$$

$$NO\_4 + NO2\_4 = y4,$$

where y1, y2, y3 and y4 are the successive pumping current values ascertained, each multiplied by a constant, and s1 is a sensitivity factor.

In some embodiments, the control unit (16) ascertains the nitrogen oxide concentration and the nitrogen oxide ratio under the assumption of linear variation in the nitrogen oxide concentration within the period of a change of mode via the following relationships:

$$NOx\_2 = y2,$$

$$F = ((y1+y3)/(2 \cdot y2))-1)/(s1-1),$$

$$NOx\_3 = (y2+y4)/2,$$

$$F = ((2 \cdot y3)/(y2+y4))-1)/(s1-1),$$

where $NOx\_2$ and $NOx\_3$ are each a nitrogen oxide concentration and $F=NO2/NOx$ is a nitrogen oxide ratio.

As another example, some embodiments include a device for ascertaining the nitrogen oxide concentration and a nitrogen oxide ratio in the exhaust gas stream from a motor vehicle, having a control unit (16) that ascertains the nitrogen oxide concentration and the nitrogen oxide ratio from at least three successive pumping current measurements.

In some embodiments, the control unit (16) ascertains the nitrogen oxide concentration and the nitrogen oxide ratio from four successive pumping current measurements.

BRIEF DESCRIPTION OF THE DRAWINGS

Further properties of various embodiments of the teachings herein are apparent from the illustrative description thereof with reference to the drawings.

DETAILED DESCRIPTION

In the methods taught by the present disclosure for ascertaining the nitrogen oxide concentration and the nitrogen oxide ratio in the exhaust gas stream from a motor vehicle, at least three pumping current measurements are ascertained successively in time in two different modes of operation of the nitrogen oxide sensor. One advantage of using at least three pumping current measurements successively in time is that the data mentioned can also be ascertained individually and accurately in dynamic operation of the motor vehicle, even though variations in the nitrogen oxide concentration and/or in the nitrogen oxide ratio can occur in this dynamic operation.

Figure 1:
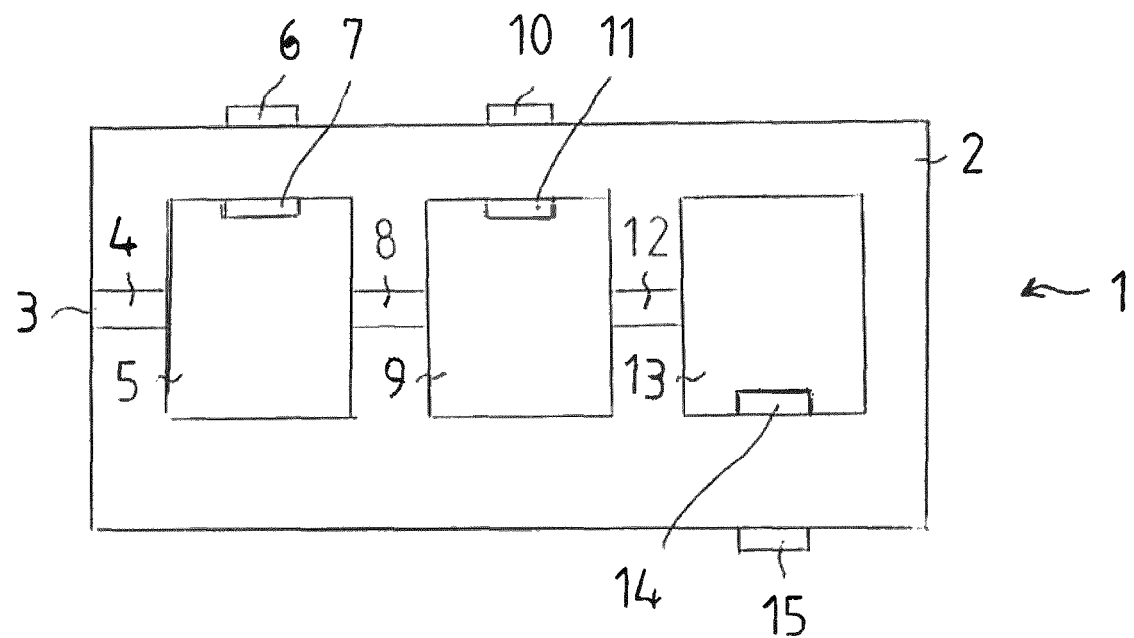
FIG. 1 a block diagram depicting a nitrogen oxide sensor that can be used to implement a method as taught herein.
Figure 1:
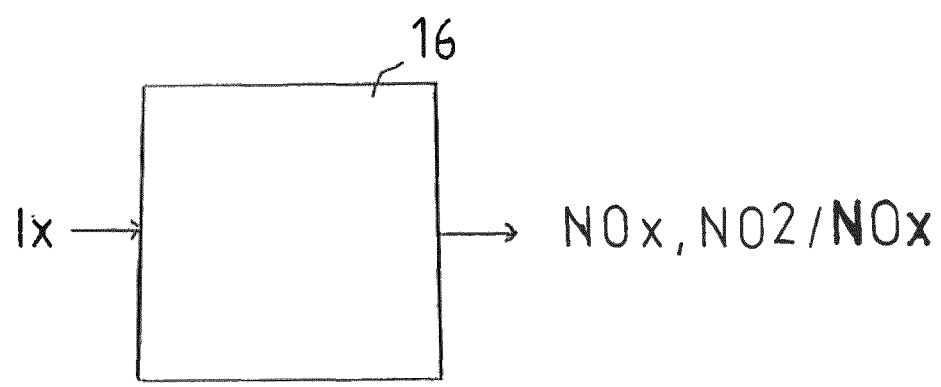

FIG. 1 shows a block diagram of a nitrogen oxide sensor that can be used to implement the methods taught herein. This nitrogen oxide sensor 1 contains a sensor body 2 having an inlet 3 for the exhaust gas stream from a motor vehicle. This inlet 3 is connected via a first diffusion pathway 4 to a first chamber 5. Assigned to the first chamber 5 are electrodes 6 and 7, to which a voltage can be applied by means of a control unit 16 in order to activate this chamber.

The outlet from the first chamber 5 is connected via a second diffusion pathway 8 to a second chamber 9 to which electrodes 10 and 11 are assigned.

The outlet from the second chamber 9 is connected via a third diffusion pathway 12 to a third chamber 13. This third chamber has assigned electrodes 14 and 15. This third chamber 13 is a measurement chamber in which a pumping current measurement can be conducted using the electrodes 14 and 15. The pumping current values Ix measured are sent to a control unit 16 that uses these pumping current measurements, in accordance with a recorded working program and using further recorded data, to ascertain the nitrogen oxide concentration and a nitrogen oxide ratio of the exhaust gas supplied to the inlet 3 of the nitrogen oxide sensor 1.

The nitrogen oxide sensor 1 shown in FIG. 1 has at least two modes of operation. In the first mode of operation, the first chamber 5 is deactivated. In this first mode of operation, the nitrogen monoxide present in the exhaust gas stream and the nitrogen dioxide present in the exhaust gas stream pass through the first chamber 5 unchanged and are supplied to the second chamber 9 via the second diffusion pathway 8. In this second chamber 9, the nitrogen dioxide present in the exhaust gas stream is converted to form nitrogen monoxide and oxygen according to the following relationship:

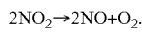

The nitrogen monoxide formed, together with the further nitrogen monoxide present in the exhaust gas stream, is passed on via the third diffusion pathway 12 into the third chamber 13. The pumping current is measured therein. The pumping current measurement is sent to the control unit 16. In addition, in the third chamber 13, the nitrogen monoxide is converted to nitrogen and oxygen, which are released to the environment via the tailpipe of the exhaust gas conduit of the motor vehicle.

In the second mode of operation, the first chamber 5 is activated. In this second mode of operation, the nitrogen dioxide present in the exhaust gas stream is already converted in the first chamber 5 to form nitrogen monoxide and oxygen according to the following relationship:

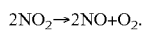

The nitrogen monoxide formed, together with the further nitrogen monoxide present in the exhaust gas stream, is passed on via the second diffusion pathway 8 into the second chamber 9. The nitrogen monoxide supplied to the second chamber 9 passes through the second chamber 9 unchanged and is supplied via the third diffusion pathway to the third chamber 13. The pumping current is measured therein. The pumping current measurement is sent to the control unit 16. In addition, in the third chamber 13, the nitrogen monoxide is converted to nitrogen and oxygen, which are released to the environment via the tailpipe of the exhaust gas conduit of the motor vehicle.

The pumping current values measured in the two modes of operation described are different on account of the different coefficients of diffusion of nitrogen dioxide and nitrogen monoxide. This pumping current differential is ascertained in the control unit 16 and, taking additional account of operating software recorded and further data recorded, used to ascertain the nitrogen oxide concentration and a nitrogen oxide ratio in the exhaust gas stream.

For this ascertainment of the nitrogen oxide concentration and the nitrogen oxide ratio, at least three successive pumping current measurements are used, where every two successive pumping current measurements are measured in different modes of operation of the nitrogen oxide sensor.

In the case of use of three pumping current measurements, for example, the first pumping current measurement is measured in the first mode of operation, the second pumping current measurement in the second mode of operation, and the third pumping current measurement in the first mode of operation again.

In some embodiments, in the case of use of three pumping current measurements, the first pumping current measurement can be measured in the second mode of operation, the second pumping current measurement in the first mode of operation, and the third pumping current measurement in the second mode of operation again.

In the case of use of four pumping current measurements, for example, the first pumping current measurement is measured in the first mode of operation, the second pumping current measurement in the second mode of operation, the third pumping current measurement in the first mode of operation again, and the fourth pumping current measurement in the second mode of operation again.

In some embodiments, in the case of use of four pumping current measurements, the first pumping current measurement can be measured in the second mode of operation, the second pumping current measurement in the first mode of operation, the third pumping current measurement in the second mode of operation again, and the fourth pumping current measurement in the first mode of operation again.

Use of at least three successive pumping current measurements achieves the effect that, even in the case of dynamic operation in which the nitrogen oxide concentration and/or the nitrogen oxide ratio vary within a short time, the nitrogen oxide concentration and the nitrogen oxide ratio can be ascertained with high accuracy.

In the case of ascertainment of the nitrogen oxide concentration and the nitrogen oxide ratio from four successive pumping current measurements, the ascertainment is based on the following relationships:

$$NO\_2 + s1 \cdot NO2\_1 = y1, \quad (1a)$$

$$NO\_2 + NO2\_2 = y2, \quad (2a)$$

$$NO\_3 + s1 \cdot NO2\_3 = y3 \quad (3a) \text{ and}$$

$$NO\_4 + NO2\_4 = y4, \quad (4a)$$

where y1, y2, y3 and y4 are the successive pumping current measurements ascertained, each multiplied by a constant. y1 and y3 were determined here in the first mode of operation, and y2 and y4 in the second mode of operation. s1 is a sensitivity factor.

Since the nitrogen monoxide concentration and the nitrogen dioxide concentration can change rapidly in the event of a change in the engine operating point, but the nitrogen oxide ratio NO2/NOx changes slowly, the nitrogen oxide concentration NOx and the nitrogen oxide ratio NO2/NOx are chosen as variables in order to use the pumping current values measured to accurately ascertain the nitrogen oxide concentration and the nitrogen oxide ratio.

Rearranged for NOx and with F=NO2/NOx, the following relationships are applicable to the above-cited relationships (1a), (2a), (3a) and (4a):

$$(1-F) \cdot NOx\_1 + s1 \cdot F \cdot NOx\_1 = y1 \quad (1b)$$

$$(1-F) \cdot NOx\_2 + F \cdot NOx\_2 = y2 \quad (2b)$$

$$(1-F) \cdot NOx\_3 + s1 \cdot F \cdot NOx\_3 = y3 \quad (3b) \text{ and}$$

$$(1-F) \cdot NOx\_2 + F \cdot NOx\_2 = y4. \quad (4b)$$

Assuming that the nitrogen oxide concentration may vary in a linear manner within the short period of a change of mode, the above relationships can be resolved as follows:

$$NOx\_2 = y2 \quad (5)$$

$$F = ((y1+y3)/2y2))-1)/(s1-1) \quad (6)$$

$$NOx\_3 = (y2+y4)/2 \quad (7)$$

$$F = ((2 \cdot y3)/(y2+y4))-1)/(s1-1) \quad (8).$$

Consequently, the relationships reproduced above can be used in the sequence specified alternately for the first mode of operation and the second mode of operation for exact ascertainment of the nitrogen oxide concentration and the nitrogen oxide ratio NO2/NOx in the exhaust gas from a motor vehicle. The accuracy of the ascertainment is based more particularly on an introduction of the nitrogen oxide ratio NO2/NOx as a variable and the ascertainment of the nitrogen oxide concentration NOx and of the nitrogen oxide ratio NO2/NOx by including at least a third pumping current value in the ascertainment of the data mentioned.

In some embodiments, it is also possible to use the nitrogen oxide ratio NO/NOx or the nitrogen oxide ratio NO2/NO as a variable. In addition, it is possible to use the nitrogen oxide ratio NO2/NOx to ascertain other nitrogen oxide ratios, for example NO/NOx or NO2/NO.

Figure 2:
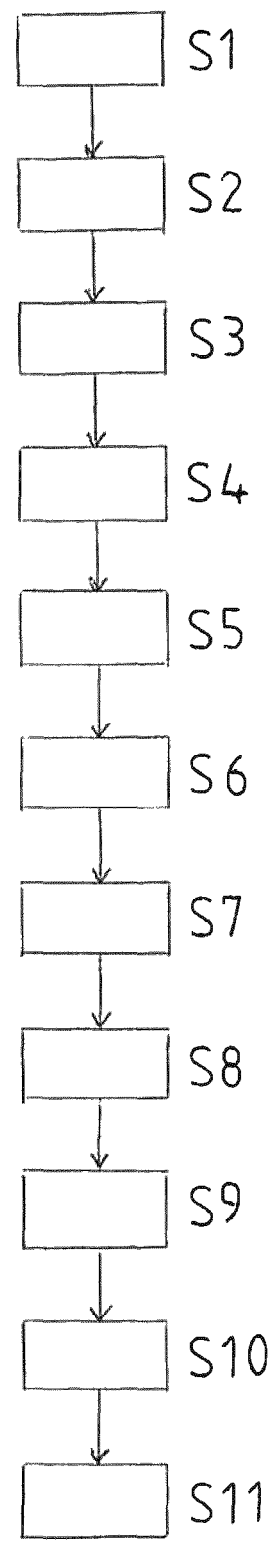
FIG. 2 a flow diagram for elucidation of a working example of a method incorporating teachings of the present disclosure.

FIG. 2 shows a flow diagram of a working example of a method of ascertaining the nitrogen oxide concentration and a nitrogen oxide ratio in the exhaust gas stream from a motor vehicle.

The method begins with a step S1.

Thereafter, in a step S2, the nitrogen oxide sensor is switched over into the first mode of operation in which the first chamber 5 is deactivated. This is followed, in a step S3, by a measurement of the pumping current in the third chamber 13, and the pumping current value measured is passed onward to the control unit 16.

The method then moves to step S4 in which the nitrogen oxide sensor is switched over into the second mode of operation in which the first chamber 5 is activated. This is followed, in a step S5, by a measurement of the pumping current in the third chamber 13, and the pumping current value measured is passed onward to the control unit 16.

Thereafter, the method moves to step S6 in which the nitrogen oxide sensor is switched over into the first mode of operation in which the first chamber 5 is deactivated. After this switchover, in a step S7, the pumping current is measured in the third chamber 13, and the pumping current value measured is passed onward to the control unit 16.

The method then moves to step S8 in which the nitrogen oxide sensor is switched over into the second mode of operation in which the first chamber 5 is activated. This is followed, in a step S9, by a measurement of the pumping current in the third chamber 13, and the pumping current value measured is passed onward to the control unit 16.

After step S9, the method moves to a step S10 in which the control unit 16 ascertains exact values for the nitrogen oxide concentration NOx and the nitrogen oxide ratio F=NO2/NOx of the exhaust gas stream according to the above-stated relationships 5, 6, 7 and 8 using the pumping current values measured, a recorded working program and further data recorded.

The method ends with a subsequent step S11.

The invention claimed is:

1. A method of ascertaining the nitrogen oxide concentration and a nitrogen oxide ratio in the exhaust gas stream from a motor vehicle, the method comprising:
   measuring a pumping current; and
   ascertaining the nitrogen oxide concentration and the nitrogen oxide ratio from at least three successive pumping current measurements.

2. The method as claimed in claim 1, wherein every two successive pumping current measurements are measured in alternating first and second modes of operation of a nitrogen oxide sensor, the first mode of operation including supplying the exhaust gas through a first chamber while deactivated, and the second mode of operation including supplying the exhaust gas stream through the first chamber while activated.

3. The method as claimed in claim 1, wherein:
the successive pumping current measurements are measured by means of a nitrogen oxide sensor having an inlet for an exhaust gas stream and three chambers arranged in series; and
every two successive chambers are connected to one another via a diffusion pathway.

4. The method as claimed in claim 3, wherein in a first mode of operation:
nitrogen monoxide present in the exhaust gas stream and nitrogen dioxide present in the exhaust gas stream pass through the first chamber unchanged and are supplied to the second chamber via a diffusion pathway;
the nitrogen dioxide present in the exhaust gas stream is converted to nitrogen monoxide in the second chamber;
the nitrogen monoxide is supplied together with the nitrogen monoxide present in the exhaust gas stream to the third chamber via a further diffusion pathway; and
a corresponding pumping current value is measured in the third chamber.

5. The method as claimed in claim 3, wherein, in a second mode of operation:
nitrogen dioxide present in the exhaust gas stream is converted to nitrogen monoxide in the first chamber;
the nitrogen monoxide is supplied together with nitrogen monoxide present in the exhaust gas stream to the second chamber via a diffusion pathway;
the nitrogen monoxide supplied to the second chamber passes through the second chamber and is supplied to the third chamber via a further diffusion pathway; and
a corresponding pumping current value is measured in the third chamber.

6. The method as claimed in claim 1, wherein the nitrogen oxide concentration and the nitrogen oxide ratio are ascertained by a control unit supplied with the at least three successive pumping current measurements.

7. The method as claimed in claim 6, wherein the control unit ascertains the nitrogen oxide concentration and the nitrogen oxide ratio from four successive pumping current measurements, the first and third of which are measured in a first mode of operation and the second and fourth of which are measured in a second mode of operation;
wherein the first mode of operation includes supplying the exhaust gas through a first chamber while deactivated, and the second mode of operation includes supplying the exhaust gas stream through the first chamber while activated.

8. The method as claimed in claim 7, wherein the control unit ascertains the nitrogen oxide concentration and the nitrogen oxide ratio on the basis of the following relationships:

$$NO\_1 + s1 \cdot NO2\_1 = y1,$$

$$NO\_2 + NO2\_2 = y2,$$

$$NO\_3 + s1 \cdot NO2\_3 = y3 \text{ and}$$

$$NO\_4 + NO2\_4 = y4,$$

where y1, y2, y3, and y4 are the successive pumping current values ascertained, each multiplied by a constant, and s1 is a sensitivity factor;
NO_1 is a nitrogen monoxide concentration measured in the first pumping current measurement, NO2_1 is a nitrogen oxide concentration measured in the first pumping current measurement;
NO_2 is a nitrogen monoxide concentration measured in the second pumping current measurement, NO2_2 is a nitrogen oxide concentration measured in the second pumping current measurement;
NO_3 is a nitrogen monoxide concentration measured in the third pumping current measurement, NO2_3 is a nitrogen oxide concentration measured in the third pumping current measurement; and
NO_4 is a nitrogen monoxide concentration measured in the fourth pumping current measurement, NO2_4 is a nitrogen oxide concentration measured in the fourth pumping current measurement.

9. The method as claimed in claim 7, wherein the control unit ascertains the nitrogen oxide concentration and the nitrogen oxide ratio under the assumption of linear variation in the nitrogen oxide concentration within the period of a change of mode via the following relationships:

$$NOx\_2 = y2,$$

$$F = ((y1+y3)/2 \cdot y2)) - 1)/(s1-1),$$

$$NOx\_3 = (y2+y4)/2,$$

$$F = ((2 \cdot y3)/(y2+y4)) - 1)/(s1-1),$$

where NOx_2 and NOx_3 are each a nitrogen oxide concentration and F=NO2/NOx is a nitrogen oxide ratio; and
where y1, y2, y3, and y4 are the successive pumping current values ascertained, each multiplied by a constant, and s1 is a sensitivity factor.

10. A device for ascertaining the nitrogen oxide concentration and a nitrogen oxide ratio in the exhaust gas stream from a motor vehicle, the device comprising:
a meter measuring a pumping current; and
a control unit ascertaining the nitrogen oxide concentration and the nitrogen oxide ratio from at least three successive pumping current measurements.

11. The device as claimed in claim 10, wherein the control unit ascertains the nitrogen oxide concentration and the nitrogen oxide ratio from four successive pumping current measurements.

* * * * *